United States Patent [19]

Lee et al.

[11] Patent Number: 5,284,660
[45] Date of Patent: * Feb. 8, 1994

[54] DELAYED ONSET TRANSDERMAL DELIVERY DEVICE

[75] Inventors: Eun Soo Lee, Redwood City; Felix Theeuwes, Los Altos; Patrick S. L. Wong, Palo Alto; Su Il Yum; Robert M. Gale, both of Los Altos; Alejandro Zaffaroni, Atherton, all of Calif.

[73] Assignee: Alza Corporation, Palo Alto, Calif.

[*] Notice: The portion of the term of this patent subsequent to Aug. 25, 2009 has been disclaimed.

[21] Appl. No.: 933,423

[22] Filed: Aug. 21, 1992

Related U.S. Application Data

[63] Continuation-in-part of Ser. No. 271,122, Nov. 14, 1988, Pat. No. 5,141,750, which is a continuation of Ser. No. 874,263, Jun. 13, 1986, abandoned.

[51] Int. Cl.5 ............................................. A61F 13/00
[52] U.S. Cl. .................................... 424/449; 424/447; 424/448
[58] Field of Search ........................ 424/448, 449, 447

[56] References Cited

U.S. PATENT DOCUMENTS

| | | | |
|---|---|---|---|
| 3,598,122 | 8/1971 | Zaffaroni | 128/268 |
| 3,598,123 | 8/1971 | Zaffaroni | 128/268 |
| 3,742,951 | 11/1982 | Zaffaroni | 128/268 |
| 3,923,939 | 12/1975 | Baker et al. | 264/49 |
| 3,948,262 | 4/1976 | Zaffaroni | 128/268 |
| 4,031,894 | 6/1977 | Urquhart et al. | 128/268 |
| 4,144,317 | 3/1979 | Higuchi et al. | 424/21 |
| 4,201,211 | 5/1980 | Chandrasekaran et al. | 128/268 |
| 4,286,592 | 9/1981 | Chandrasekaran | 128/260 |
| 4,314,557 | 2/1982 | Chandrasekaran | 128/260 |
| 4,379,454 | 4/1983 | Campbell et al. | 604/897 |
| 4,568,343 | 2/1986 | Leeper et al. | 604/896 |
| 4,655,766 | 4/1987 | Theeuwes et al. | 604/896 |
| 4,781,924 | 11/1988 | Lee et al. | 424/449 |
| 4,837,027 | 6/1989 | Lee et al. | 424/449 |
| 4,917,895 | 4/1990 | Lee et al. | 424/448 |
| 5,004,610 | 4/1991 | Osborne et al. | 424/448 |
| 5,071,656 | 12/1991 | Lee et al. | 424/448 |
| 5,141,750 | 8/1992 | Lee et al. | 424/448 |

*Primary Examiner*—Thurman K. Page
*Assistant Examiner*—Jyothsna Venkat
*Attorney, Agent, or Firm*—Jacqueline S. Larson; Jean M. Duvall; Paul L. Sabatine

[57] ABSTRACT

A diffusional drug delivery device is described which can provide for delayed onset of therapeutic effect and for delivery of the therapeutic agent in predetermined temporal patterns at optimum rates. Delay means are provided between the agent reservoir and the surface through which the agent is released by diffusion to delay the release of agent at a therapeutic rate for predetermined times after application. Suitable means include a delay membrane disposed between the releasing surface and the agent reservoir, which membrane is preferably free of undissolved agent and/or is initially impermeable to the agent and thereafter becomes permeable. One or more agent chambers defined by one or more of such membranes may be provided, whereby agents are released in predetermined temporal patterns at optimal release rates. Delayed permeability enables programmed washout periods to be obtained from the sequential and concurrent application of devices for the administration of drugs, such as nitrates, to which patients may develop a tolerance on continuous administration over extended time periods.

27 Claims, 2 Drawing Sheets

DELAYED ONSET TRANSDERMAL DELIVERY DEVICE

RELATED APPLICATIONS

This application is a continuation-in-part of U.S. patent application Ser. No. 07/271,122, filed Nov. 14, 1988, now U.S. Pat. No. 5,141,750, which is a continuation of U.S. application Ser. No. 06/874,263, filed Jun. 13, 1986, now abandoned. This application is also related to U.S. Pat. No. 5,071,656, which is a continuation of U.S. application Ser. No. 06/874,263, referred to above. All of these applications are commonly assigned to ALZA Corporation.

FIELD OF THE INVENTION

The invention relates to diffusional drug delivery devices, and more particularly to such devices which release drugs at predetermined intervals after being placed at the site of administration.

BACKGROUND OF THE INVENTION

Illustrative examples of diffusional drug delivery devices are found in U.S. Pat. Nos. 3,598,122, 3,598,123, 3,742,951, 3,948,262, 4,031,8942 4,144,317, 4,201,211, 4,286,592, 4,314,557, 4,379,454, and 4,568,343, for example, which are incorporated herein by reference. In these devices, a drug or other active agent is released by diffusion from a reservoir through the agent-releasing surface of the device to the biological environment at which the device is applied. Such devices perform well in the administration of many agents but are not suitable for the administration of an agent whose dosage regime requires that the onset of therapeutic effect be delayed for a significant period of time after application of the device at the site of delivery. This is because the surface through which the agent is released, at the time of application, contains the agent in an amount that is significant compared to the amount in the body that gives rise to a therapeutic concentration. In those devices which utilize an agent reservoir which contains an agent at a concentration above the saturation concentration of the agent in the material from which the reservoir is formed, the agent will be present at the agent-releasing surface at the saturation concentration of the agent in the material from which the releasing surface is formed. Saturation concentration is equivalent to a thermodynamic activity of 1 (unit activity). When prior art diffusional devices are applied, agent is immediately available for diffusion into the body and the concentration of the agent at the releasing surface rapidly decreases as the concentration gradient required for steady-state diffusional delivery is established by the absorption of the agent from the releasing surface into the body. In some cases the initial rate of release is unacceptably high, and a method for reducing this initial "burst" of agent delivery is described in U.S. Pat. No. 3,923,939 to Baker et al. Even in the Baker patent, the agent-releasing surface of the diffusional embodiment contains the agent at the saturation concentration of the agent in the material in which it is dispersed, and delivery commences immediately in the manner described above.

Non-diffusional devices are known which do not immediately present drug to the biological environment when installed, such as devices which contain material in breakable microcapsules or have a fluid-imbibing pump described in commonly assigned U.S. Pat. No. 4,655,766. Diffusional delivery devices known to the prior art, however, do not possess this capability.

One of the advantages of a continuous release dosage form, such as a transdermal drug delivery device, is the improvement in patient compliance that is obtained from the concurrent removal of one device and application of a new device at the same time. This advantage is lost when removal and application occur at different times or where onset of a therapeutic effect is desired at an inconvenient time such as shortly prior to awakening. It is not possible, using concurrent application and removal of diffusional delivery devices of the prior art to substantially delay the onset of transdermal drug delivery from the time of application, such as at bedtime, until a later, often inconvenient, time, such as shortly prior to awakening. While other, non-diffusional delivery devices exist which can deliver drug after an extended delay, diffusional devices of the prior art do not possess this capability and rapidly commence delivering the drug at their intended therapeutic rates.

There is, therefore, a continuing need to provide a diffusional agent delivery device which provides for delayed onset of active agent administration and release of active agent at the desired rate at a predetermined interval after application.

SUMMARY OF THE INVENTION

The present invention provides a diffusional device for the delivery of active agents, such as drugs or other biologically active agents, in a controlled and preprogrammed manner. The devices of this invention are particularly useful in providing a predetermined, delayed onset of therapeutic effect for any desired time period after application to the skin. Thus, a device could be removed and a new one applied simultaneously, wherein the desired drug-free interval is obtained.

A diffusional delivery device, in its broadest sense, comprises an active agent reservoir from which agent passes by diffusion to the active agent-releasing surface of the device and from there into the biological environment to which it is applied. In certain embodiments of the invention, one or more delay membranes are disposed between the agent reservoir and the surface through which the agent is released from the device to produce a delayed onset of agent administration at the intended therapeutic rate. The delay membrane is substantially free of undissolved agent and may be formed from a material which in a first state has a low permeability, and in a second state has a high permeability to the agent whose release is being delayed. Typically, there will be at least a factor of two, and preferably at least an order of magnitude, difference in the permeability between the first and second states. In a presently particularly preferred embodiment, liquid triggers the change of state.

Certain embodiments of this invention possess unique characteristics by which they may be readily distinguished from other diffusional delivery devices. As discussed above, when conventional diffusional devices are placed into operation, the concentration of the agent at the agent-releasing surface decreases as the agent at the surface is absorbed by the body. According to certain embodiments of the present invention, however, the concentration of the agent at the agent-releasing surface actually increases after the device is placed into operation. This occurs because the delay membrane functions to maintain the initial concentration of the agent at the releasing surface of the device substantially below the concentration which will exist when the device is operating at its intended steady-state agent delivery rate.

Another characteristic by which certain embodiments of this invention may be distinguished from other diffusional delivery devices has to do with the concentration or loading of active agent at the active agent-releasing surface. As noted above, it is desired, in certain embodiments, that, in its first state, the delay membrane be very impermeable to the agent being delayed. Nevertheless, it must be recognized that nothing is absolutely impermeable and even in preferred embodiments there may be small concentrations of the agent at the releasing surface. Typical delay membranes which undergo a change of state exhibit an extremely low solubility and diffusivity for the agent in their first state. As a result, even if the delay membrane has reached equilibrium with the reservoir, and may be at a thermodynamic activity of unity, the actual concentration or loading of the agent at the releasing surface will be too low to be capable of sustaining a therapeutically effective delivery rate. Thus, if the delay membrane is the agent-releasing surface of the device, the small amount of agent at the surface will be rapidly absorbed into the body at the time of application and agent will not be available until the membrane changes state and the concentration is allowed to increase as described above.

A similar condition will exist even if there is another layer, such as an adhesive, which has a high solubility for the active agent and which is disposed between the delay membrane and the body. If such a device were allowed to sit for a time sufficient to reach equilibrium (when the thermodynamic activity in the reservoir, delay membrane and adhesive are the same), then the concentration of the agent in the adhesive would be substantially higher than in the delay membrane. If, however, the thickness of the adhesive is small, the actual amount of agent available for immediate administration is likewise small. This small amount will be rapidly absorbed as described above and will not be replenished until the delay membrane changes state or otherwise passes agent at the higher, therapeutically effective rates. This condition is addressed according to this invention by, for example, keeping the adhesive layer thin, establishing a shelf life for the product which is sufficiently short with respect to the time to reach equilibrium concentration so that the concentration in the adhesive layer is kept low, or a combination thereof.

Accordingly, the agent-releasing surfaces of certain embodiments of our invention are characterized by being substantially free of agent at the time they are applied to the body. As used herein, the term "substantially free of agent" means either free of agent or containing an amount of agent insufficient to establish and maintain therapeutically effective agent delivery rates at the time of application to the delivery site.

As used herein, the term "therapeutically effective" rate or amount refers to a rate or amount of active agent that provides a therapeutic or beneficial result or effect.

As used herein, the terms "drug", "agent" and "active agent" are used interchangeably and are intended to have their broadest interpretation as any therapeutically active substance which is delivered to a living organism to produce a desired, usually beneficial, effect.

In accordance with one embodiment of the invention, a device suitable for transdermal administration has a backing layer which is not permeable to the agent to be delivered. Agent is contained in a reservoir contiguous to the backing layer. The agent may be in solution, in combination with other components, in suspension, or in powder form. A delay membrane is disposed contiguous to the agent reservoir. In one state, the delay membrane is not permeable to the agent, whereby the agent cannot diffuse from the device. In another state, the delay membrane is permeable to the agent, and will permit diffusion of the agent at the desired rate.

In accordance with a preferred embodiment of the invention, the delay membrane is activated by moisture, such as is readily available from the site of administration such as the cutaneous surface, particularly in occluded regions. The delay membrane may alternatively be moistened by dipping into a liquid immediately prior to application. Water serves as the activating liquid where the membrane is a hydrophilic polymer. Other liquids, such as ethanol, can change the permeability of particular membranes.

Preferred delay membrane polymers are hydrophilic or semihydrophilic polymers, including polyvinyl alcohol, polyvinyl pyrrolidone, hydroxypropylcellulose, hydroxyethylcellulose and hydroxypropylmethylcellulose. The backing layer and membrane may be heat sealed, where the membrane polymer is fabricated with integral plasticizer. Alternatively, layers are fastened with an adhesive, such as a polyisobutylene copolymer, or silicone-based adhesives.

In accordance with another embodiment of the invention, activatible delay membranes form chambers, which separate components until activated. In one embodiment, incompatible agents are prevented from interacting by a membrane barrier. Alternatively, other agents which act upon the active agent are stored within a chamber until activation, whereupon the agents are mutually exposed. In another embodiment, active agents to be released at different times are provided in separate, non-coplanar chambers.

In accordance with yet another aspect of the invention, the hydrophilic delay membrane is laminated with heat-sealable material, such as polyethylene, whereby the backing layer and laminate are heat-sealed to enclose an active agent reservoir.

In accordance with yet another embodiment of the invention, a device is installed which presents no drug to the biological environment when initially installed, and which delivers drug by diffusion after a delay.

DETAILED DESCRIPTION OF THE INVENTION AND THE PREFERRED EMBODIMENTS

With reference to the Figures, which are not drawn to scale, the devices shown represent, for purposes of illustration, transdermal delivery devices because these are preferred embodiments of this invention. It must be recognized, however, that this invention is applicable to delivery devices generally and in non-transdermal application certain components such as adhesives and backing layers can be omitted. A transdermal delivery device according to this invention may include an active agent-impermeable backing member, an active agent reservoir, and a delay membrane which in a first state is impermeable to the active agent and in a second state is permeable to the active agent. The delay membrane may be a glassy polymer which blocks agent diffusion to the skin and which, in the presence of moisture, swells by absorbing water, becoming permeable to the agent.

Figure 1:
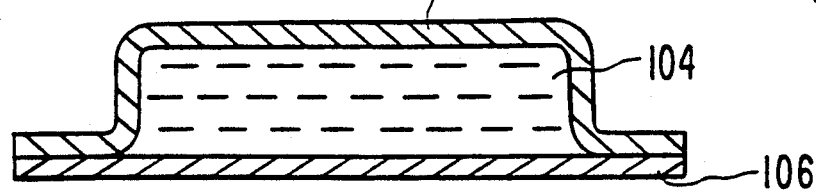
FIG. 1 illustrates in cross section a delivery device of the present invention having a single agent reservoir and delay membrane.

Transdermal device 100, shown in FIG. 1, includes an active agent-impermeable backing support layer 102, an active agent reservoir 104, and a delay membrane 106. When maintained in contact with a wearer's skin by an adhesive overlay or a belt, buckle or elastic band (not shown), for example, delay membrane 106 undergoes a change of state whereby the permeability of membrane 106 to the active agent and the concentration of the agent therein both start to increase.

Backing support layer 102 is not permeable to the active agent. Appropriate materials are known to the art and include, but are not limited to, metallized polyester films, polyethylene or polypropylene. Active agent reservoir 104 contains the skin-permeable drug or other active agent desired to be delivered, dissolved or dispensed in a carrier therefor. Agent reservoir 104 also may contain stabilizing agents, thickeners, permeation enhancers or other additives as are known to the art.

Delay membrane 106 is preferably substantially free of undissolved active agent and is fabricated from a material which is impermeable to the agent in a first state such as dry or cold, for example, and permeable to the agent in a corresponding second state such as wet or warm. Glassy, hydrophilic polymers which become permeable upon exposure to water are presently preferred for certain embodiments because sufficient water for causing the change of state is normally available from skin, particularly when it is occluded.

Examples of materials suitable as a delay membrane include polyvinyl alcohol (PVA), polyacrylamide, hydroxypropylmethylcellulose (HPMC), hydroxypropylcellulose, hydroxyethylcellulose, hydroxymethylcellulose, polyacrylic acid, polyvinyl pyrrolidone (PVP), and hydroxyethylmethacrylate (HEMA). Albumin, gelatin and cellulose may also be used. Additionally, delay membranes which are activated by non-aqueous agents may be provided. Activation is achieved by immersing the device in the liquid, such as ethanol, water or phosphate-buffered saline, or by providing isolated releasable liquid within the device. Other mechanisms by which the delay membrane can be controllably converted from an impermeable to a permeable state are within the scope of this invention.

Figure 2:
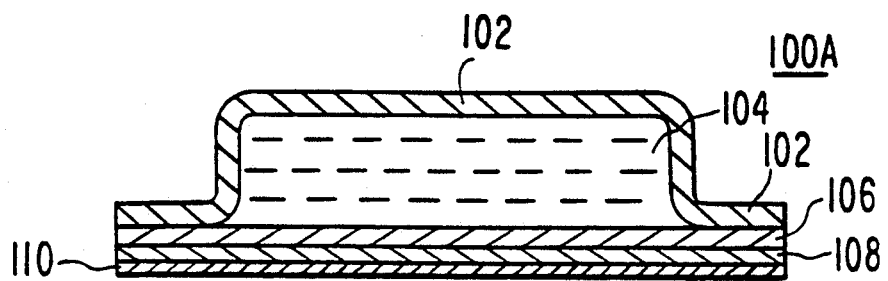
FIG. 2 is a device as in FIG. 1, but further including a rate-controlling layer and an adhesive layer.

Device 100A, shown in FIG. 2, has a rate-controlling membrane 108 disposed in combination with delay membrane 106. Rate-controlling membrane 108 may control the release rate of active agent from the device, the rate of imbibition of the activating fluid into the device, or both. If rate-controlling membrane 108 controls the release rate of agent, either delay membrane 106 or rate-controlling membrane 108 may be positioned in abutting conformity to active agent reservoir 104. If rate-controlling membrane 108 controls the rate of water imbibition into the device, and thus the time required to cause delay membrane 106 to change state, it should be positioned as shown in FIG. 2. Rate-controlling membrane 108 may be fabricated from permeable, semipermeable or microporous materials which are known to the art to control the rates of agents or fluids into and out of delivery devices.

Lamina 110 is an adhesive layer which, in accordance with one embodiment, contains a predetermined amount of drug which serves to saturate the skin for more rapid therapeutic effects where desired. Silicone compounds are commonly used as adhesives; however, numerous materials are known which possess the requisite strength and skin compatibility. An adhesive overlay or other means for maintaining the device on the skin can be employed instead of, or in combination with, adhesive lamina 110.

Figure 3:
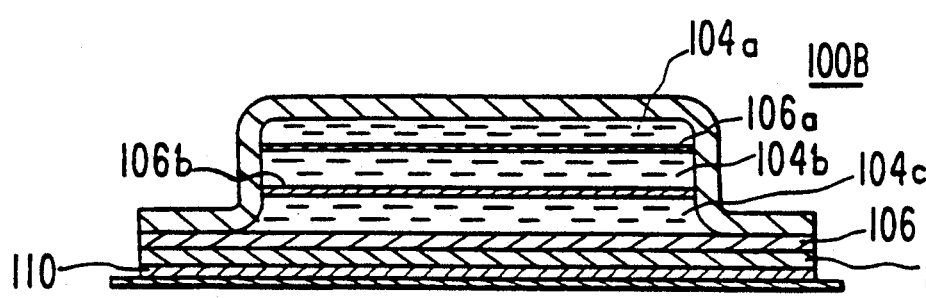
FIG. 3 illustrates a multi-agent device according to the invention having three delay membranes.

In FIG. 3, an alternative device 100B has a plurality of active agent reservoirs 104a, 104b and 104c separated by delay membranes 106a and 106b. The agents in reservoirs 104a, 104b and 104c may be the same or they may be different or one reservoir may contain an agent different from that in the other two reservoirs, depending upon the therapeutic regime desired. Membrane 106a prevents mixing of active agent in reservoirs 104a and 104b, while membrane 106b separates active agent in reservoirs 104b and 104c. The membranes may also have the same or different thickness depending upon the temporal delivery pattern desired and, as shown, membrane 106b has a greater thickness than that of membrane 106a. Rate-controlling membrane 108 may control the rate of water imbibition into device 100B so that activation of delay membranes 106a and 106b can be delayed substantially beyond the activation of delay membrane 106 to provide for sequential delivery of the active agents in the three agent layers.

In operation, water migrates into device 100, 100A or 100B from the skin surface or other source, typically by osmosis or diffusion, passing through intervening adhesive lamina 110, if present, rate-controlling membrane 108, if any, and then to delay membrane 106. Upon contact with the water, delay membrane 106 becomes progressively more permeable to the active agent. As the delay membrane becomes permeable, active agent in reservoir 104 or 104c diffuses through rate-controlling layer 108, and thence through adhesive lamina 110 to the skin surface. As water passes to delay membranes 106b and 106a at a rate established by rate-controlling membrane 108, they, in turn, become more permeable to the active agents and the agents are sequentially released from layers 104b and 104a, respectively. As the delivery rates of the agents in each of the reservoirs increase towards their steady-state rates, the concentration of that agent in adhesive layer 110 also increases. It has been demonstrated that delay membranes require a longer hydration time period as thickness is increased. Accordingly, delay membrane 106a will activate more rapidly than delay membrane 106b if the same material is used in both membranes.

Figure 4:
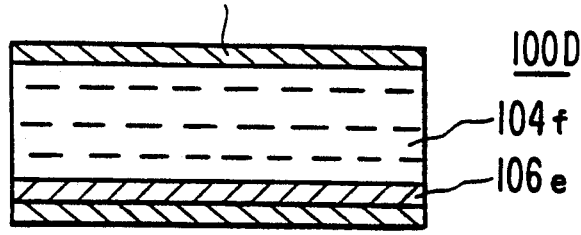
FIG. 4 illustrates in cross section another delivery device according to the invention.
Figure 5:
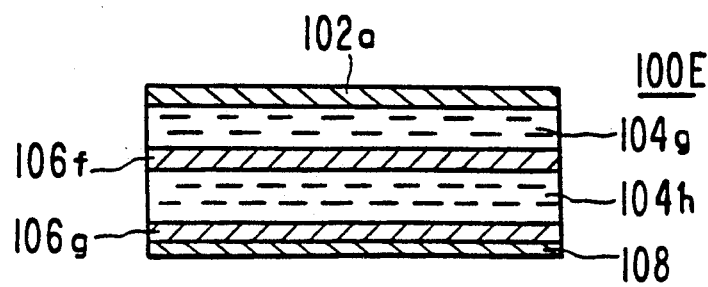
FIG. 5 illustrates a two-agent, two-membrane, non end-sealed device according to the present invention.

FIGS. 4 and 5 illustrate laminated devices 100D and 100E, respectively, according to this invention. These devices are not end-sealed. Each of devices 100D and 100E has a backing layer 102a. Active agent reservoir laminae 104f, 104g and 104h may, in addition to permeation enhancers and stabilizing agents, contain rheological modifiers, viscosity boosters or thixotropic/gelling agents to prevent flow of the agent matrix beyond the device confines. Delay membranes 106e, 106f and 106g do not flow, as these membranes, generally, have a rigid, glass-like rheology when dry. When moistened, or wet, the delay membranes continue to retain integrity.

The device of FIG. 4 is suitable for delaying the onset of therapeutic effect for a period of time after application. The device of FIG. 5 illustrates a configuration which is capable of delivering two active agents sequentially or, if the same agent is contained in reservoirs 104g and 104h, capable of providing a predetermined interruption in administration coupled with a predetermined delay in therapeutic onset. By concurrently applying a fresh device and removing the exhausted device at the same time each day or every other day, for example, a complex repetitive pattern of agent administration can be obtained with a high degree of patient compliance. Thus, if nicotine were the drug delivered in the embodiments of FIGS. 4 and 5, periodic periods of no nicotine would be experienced by the patient during those times, such as during sleep, when the patient does not require the drug. In this example, the device of FIG. 4 would be a 24-hour device and the device of FIG. 5 would be a 48-hour device. The delay membranes would be selected to produce the desired "off" periods, typically considered to be in the range of from 4–12 hours.

Figure 6:
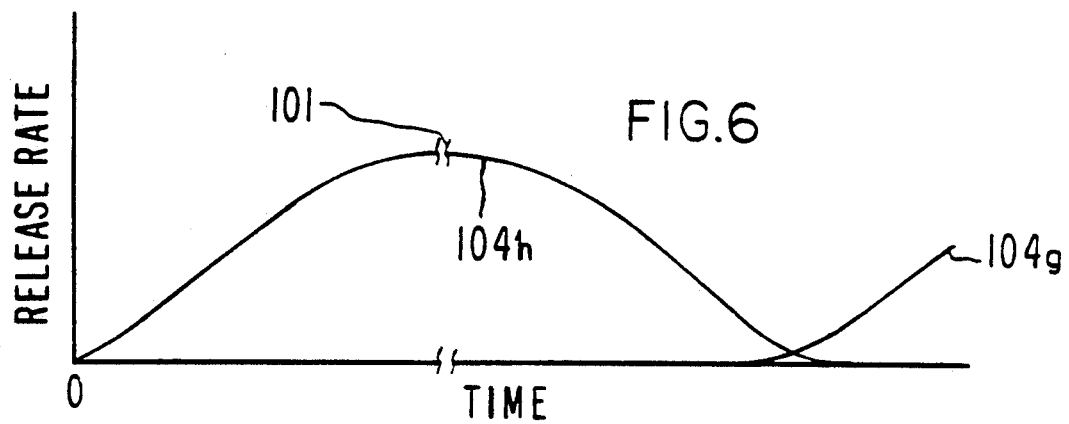
FIG. 6 is a theoretical plot of the release rate vs. time for the device shown in FIG. 5.

FIG. 6 illustrates the theoretical effect produced by device 100E in which rate-controlling membrane 108 controls both the rate of water imbibition into the device and the rate of active agent release from the device. The indicated missing time interval 101 represents the substantially constant agent release rate established by membrane 108. Rate-controlling membrane 108 is also selected to control the rate of imbibition of water so that delay membrane 106f becomes permeable to the active agent only after the amount of agent in reservoir 104h has become substantially depleted. This permits the blood levels of the agent to drop in the time period running from the end of period 101 until delivery from reservoir 104g reaches effective rates which occurs when curve 104g continues to rise, in a manner similar to curve 104h.

Typically, the devices of this invention include a removable release liner (not shown) on the device surface to be placed on the skin or mucosa, which liner is removed prior to placement. Such release liners are known to the art and are typically of siliconized paper or siliconized polymer or the like.

The present invention is particularly useful in delivering those active agents which should not be delivered in a continuous manner over a prolonged period of time. Agents which may be beneficially delivered according to this invention include agents where a therapeutic effect is desired at an inconvenient time or where no therapeutic effect is desired for a particular time period. These agents include, but are not limited to, nicotine (for providing a period of no nicotine delivery during sleep and then providing nicotine in a therapeutic amount at or just prior to awakening); caffeine (for providing delivery of caffeine in the morning hours as a means of awakening); melatonin (for providing melatonin delivery during the desired sleep cycle, normally late at night, usually between about 11:00 p.m. and 6:00 a.m.); painkillers, steroidal anti-inflammatory drugs and non-steroidal antiinflammatory drugs for relieving early morning stiffness and pain; and the cardiovascular drugs (for providing initiation of delivery early in the morning, usually at about daybreak), examples of which cardiovascular drugs are the vasodilators (examples of which are nitroglycerin, amyl nitrate and other nitrates and nitrites), the beta blockers (examples of which are propranolol, timolol and atenolol), calcium channel blockers (examples of which are nifedipine and nicardipine), and ACE inhibitors (examples of which are captopril, enalapril and enalaprilat). Other active agents which may be usefully delivered from devices according to this invention are those agents, such as morphine, methodone, secoverine and benzotropine, which cause irritation from an initial burst when delivered by prior art devices; and those agents, such as the nitrates and alcohols, that require a "washout" period or period of no agent delivery so that the patient does not build up a tolerance to the agent.

One drug which is particularly suitable for delayed delivery according to the present invention is nicotine. Transdermal delivery devices for the immediate delivery of nicotine have been recently introduced for the treatment of smoking cessation. These devices are available for delivery over 24 hours, where the patient replaces the device once every 24 hours, and for delivery over 12 hours, where the patient may either replace the device once every 12 hours or wear a device for a 12-hour period, followed by no device for 12 hours. Each of these regimens can provide drawbacks. With delivery of nicotine continuously over 24 hours (with either the 24-hour patch or two 12-hour patches), certain side effects have been reported that are associated with delivery of nicotine during sleeping hours. These include abnormal dreams and insomnia. If a device is not worn during sleep in order to reduce or eliminate these side effects, then a new nicotine patch would not be applied until after awakening in the morning. However, when no nicotine has been delivered during the night, the plasma nicotine concentrations will be low and smokers encounter early morning withdrawal symptoms such as "morning craving" and the urge to smoke. Placement of a nicotine patch after awakening will not immediately relieve these cravings, and this could greatly decrease the efficacy of the transdermal devices for stopping the smoking habit.

A delayed delivery device of the present invention can be designed to be placed on the skin at dinner time or at bedtime, for example, and would not begin delivery of nicotine to the skin until shortly prior to awakening such as one to three hours prior to awakening, usually five to eight hours after initial placement, after which time therapeutic levels of nicotine would be delivered for about the next sixteen to nineteen hours. This initial delay of nicotine delivery could reduce or eliminate the side effects of abnormal dreams and insomnia because significant drug delivery will only occur during waking hours. At the same time, efficacy will be maintained because plasma nicotine concentrations will be achieved in sufficient time prior to awakening to overcome any morning craving and the urge to smoke.

Having thus generally described the present invention, the following specific examples of the invention are provided.

EXAMPLE 1

Figure 7:
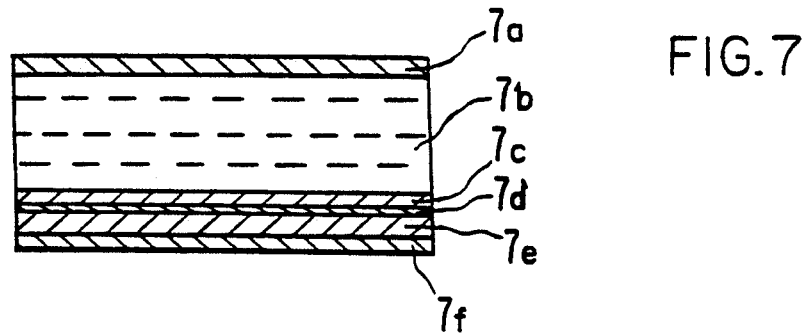
FIG. 7 illustrates in cross section another device of the present invention, which is discussed in Example 1.

Transdermal delayed delivery devices for the delayed onset of delivery of nicotine according to the present invention and illustrated in FIG. 7 were prepared as follows.

A 0.05 mm high-density polyethylene (HDPE) film is extruded onto a siliconized polyester film (for protecting the film layer until final assembly) to give the rate-controlling membrane 7c. Sixty parts of ethylene vinyl acetate copolymer ("EVA") having 40% vinyl acetate content were blended with 40 parts of nicotine base until the components were well dispersed to give the active agent reservoir 7b. This reservoir layer was then extruded through a slot die at about 50° C. onto the HDPE membrane layer at about 0.125 mm thickness. Downstream from this, a MEDPAR ® film of 0.05 mm thickness was laminated to the other side of the EVA/nicotine reservoir to give the nicotine-impermeable backing layer 7a, and the resulting composite film was taken up on a winding station.

In a separate operation, a polyisobutylene (PIB) film (85% 1,200,000 MW and 15% 35,000 MW) acrylate adhesive was solution-cast on a siliconized substrate (for protecting the adhesive until final assembly) to a dry thickness of 0.005 mm to give the adhesive tie layer 7d. Polyvinyl alcohol (PVA; 88% OH) film at 0.05 mm thickness was laminated to the adhesive layer to give the delay membrane 7e. A second acrylate adhesive layer was cast to a dry thickness of 0.05 mm on the other surface of the PVA delay membrane layer to give the contact adhesive layer 7f.

For the final assembly, the siliconized protective layers contacting the HDPE rate-controlling membrane and the adhesive tie layer were removed and the HDPE layer of the one laminate is laminated to the adhesive tie layer of the second laminate. Final delay-onset devices were then die cut and packaged for use.

EXAMPLE 2

The devices of Example 1 having a polyvinyl alcohol delay membrane were tested in vitro for nicotine release, in comparison with a prior art device (the Nicoderm ® transdermal patch). Release rates of nicotine over time through a 1.5 mil Hytrel ® membrane into an aqueous bath at 35° C. were determined, the Hytrel membrane being used because it simulates the water transport properties of human skin. For the test, the release liner was removed from each device, and each device was covered at its drug release surface with the Hytrel membrane to control water availability to the test device in all release rate tests. Each test was run over 24 hours at 35° C. The release medium was distilled water. Drug concentration was determined by UV absorption at 259 nm. When the devices were tested, the prior art devices began to release nicotine through the Hytrel membrane within a short period of time after coming into contact with the aqueous release medium, whereas the release rate of the devices of Example 1 was zero after 5 hours of contact.

It is clear from the above results that devices incorporating the delay membrane, as compared with the prior art devices, do not immediately release agent when the Hytrel membrane, which simulates the rate at which water would be available to the device from the skin to which it is intended to be applied, is exposed to the aqueous bath. This is due to the fact that the agent-releasing surfaces 7f of the embodiments of this invention were substantially free of agent when exposed to the skin whereas the corresponding surfaces 7d of the controls contain nicotine at unit thermodynamic activity. Continued delay of agent release is due to the impermeability of the delay membrane to the agent until the membrane has become hydrated.

The delay membranes are capable of in vivo operation as switches, preventing active agent release until the device is occluded and provided with sufficient moisture for activation from the skin. The controls will, in vivo, immediately present agent to the skin and commence agent delivery. Devices according to this invention, however, will all exhibit the delays shown before release at the intended steady-state rate will be achieved.

EXAMPLE 3

Transdermal delayed delivery devices for the delayed onset of delivery of melatonin according to the present invention are prepared as follows.

EVA 40 (EVA with 40% vinyl acetate) (2.7 g), glycerol monooleate (1.5 g; Myverolo ® 1899K, Eastman Chemical Products; "M-GMO") and chloroform (27.0 g) were added together in a vial. The vial was capped (Teflon ®-lined) and rotated for 4-6 hours, until the EVA 40 was dissolved. The resulting homogeneous solution was then poured onto a glass plate lined with a siliconized polyester release liner film (siliconized PET). The chloroform was evaporated off until the film was dry. Melatonin (0.35 g; Sigma Chemicals) was then dry blended into 1.98 g of the EVA 40/M-GMO dry film in a rubber mill until homogeneous. The resulting material, having a composition of 15 wt % melatonin, 30 wt % M-GMO and 55 wt % EVA 40, was melt-pressed to about 8 mil (0.2 mm) thickness between two sheets of siliconized PET release liner at 60° C. and 10,000 lbs. pressure. The resulting film was heat-laminated to an impermeable backing (Medpar ® or Scotchpak ®, for example). The drug matrix/impermeable backing laminate was then laminated, on the side opposite the impermeable backing, to an acrylic contact adhesive (2 mil; MSX 1010P, 3M) to provide a monolith with an adhesive tie layer.

In a separate operation, acrylic adhesive was solution-cast to a dry thickness of 0.05 mm on a siliconized PET release liner to give the contact adhesive layer. Polyvinyl alcohol (PVA; 88% OH) film at 0.05 mm thickness was laminated to the adhesive layer to give the delay membrane.

For the final assembly, the siliconized protective layer contacting the EVA/melatonin reservoir is removed and the exposed adhesive tie layer is adhered to the PVA layer of the second laminate. Discs of 19 CM² size each are punched or die-cut from the laminate to give final devices having 55.6 mg of melatonin per device or 2.92 mg of melatonin per CM².

Following the above procedures, melatonin devices identical to the above are manufactured, except that the delay membrane is formed from polyvinyl pyrrolidone. In like manner, melatonin devices are made having hydroxyethylcellulose delay membranes, having hydroxypropylcellulose delay membranes, and having hydroxypropylmethylcellulose delay membranes.

Devices according to FIGS. 1, 2, 3, 4, 5, and 7 may be produced by conventional pouching, laminating or extruding techniques as known to the art. In accordance with the invention, many configurations are constructable, wherein a wide variety of release-rate and delay characteristics are obtainable. Additionally, different active agents, or different concentrations of the same active agent, are released at predetermined time intervals, whereby highly therapeutic results are obtained with a minimum amount of agent. Moreover, complicated dosage patterns may be administered without dependence on patient compliance and without interruption in the patient's lifestyle.

In accordance with the above described embodiments, it can additionally be seen how the invention provides for a powerful and flexible means of programming, or coordinating, the diffusional release of one or more agents from a single device, in a single application. Physicians can prescribe a complex agent administration program with far greater assurance that the regime will be adhered to. The patient need not interrupt his/her daily routine to take medication, nor can the patient forget or become confused, with respect to the timing and types of medication which must be taken. Moreover, the amount of active agent can be reduced, since therapeutic regimen can be defined more closely with delay membranes, either alone or in combination with conventional rate-controlling membranes. By providing for agent washout, particularly with agents such as nitrates to which patients may develop a tolerance, agent efficacy is enhanced while patient compliance is maintained. Additionally, agents which have limited biological half-lives may be used in lower quantities, now that a means of repeatedly and sequentially reintroducing predetermined amounts of agent has been provided by the invention.

While this invention has been described with respect to certain specific embodiments thereof, it should not be construed as being limited thereto. Numerous modifications and substitutions will suggest themselves to workers skilled in the art and may be made without departing from the scope of this invention, which is limited only by the following claims.

What is claimed is:

1. A controlled release dispensing device for delivering a drug to skin or mucosa and adapted to delay the onset of drug delivery at a therapeutically effective rate for a predetermined time after placement of said device in drug-transferring relationship to the skin or mucosa, said device comprising, in combination:
    a drug-containing reservoir having a surface through which said drug is released to the skin or mucosa, said drug being selected form the group consisting of nicotine and melatonin; and
    a drug release delay membrane comprised of hydrophilic or semihydrophilic polymer disposed between the skin or mucosa and the releasing surface of said reservoir, said delay membrane being substantially free of undissolved drug and being impermeable to said drug in a dry state and permeable thereto in a hydrated state;
    whereby said drug must pass through said delay membrane to reach the skin or mucosa and whereby release of said drug from said reservoir to the skin or mucosa at said therapeutically effective rate is delayed until the delay membrane is converted from its dry state to its hydrated state.

2. A device according to claim 1 wherein said delay membrane is converted from its dry state to its hydrated state by cutaneous liquids.

3. A delivery device for the percutaneous administration of a drug selected from the group consisting of nicotine and melatonin and adapted to delay the onset of drug delivery at a therapeutically effective rate for a predetermined time after placement of said device in drug-transmitting relationship to the skin or mucosa, said delivery device comprising;
    a backing layer impermeable to said drug;
    a drug-containing reservoir disposed between said backing layer and the skin or mucosa;
    a drug release delay membrane comprised of a hydrophilic or semihydrophilic polymer disposed between said reservoir and the skin or mucosa such that said drug must pass through said delay membrane to reach the skin or mucosa, said delay membrane being substantially free of undissolved drug and being impermeable to said drug when in a dry state and permeable to said drug when in a hydrated state; and
    means for maintaining said device in drug-transmitting relationship to the skin or mucosa.

4. A device according to claim 3 wherein said delay membrane is converted from its dry state to its hydrated state by cutaneous liquids.

5. A device according to claim 3 which further comprises a second drug-containing reservoir disposed between said backing layer and the skin or mucosa and a second drug release delay membrane comprised of a hydrophilic or semihydrophilic polymer disposed between said second reservoir and the skin or mucosa.

6. A device according to claim 3 which further comprises a rate-controlling membrane for controlling the rate at which said delay membrane becomes hydrated when the device is placed in contact with the skin or mucosa.

7. A device according to claim 3 which further comprises a rate-controlling membrane for controlling the rate at which said drug is transmitted from said drug reservoir to the skin or mucosa.

8. A device according to claim 5 which further comprises at least one rate-controlling membrane.

9. A device according to claim 3 wherein said means for maintaining said device to the skin or mucosa comprises a contact adhesive disposed between said delay membrane and the skin or mucosa.

10. A device according to claim 9 wherein the total loading of drug in said contact adhesive at the time of application to the skin or mucosa is insufficient to establish and maintain drug delivery at a therapeutic rate.

11. A device according to claim 3 which further comprises an adhesive tie layer interposed between said delay membrane and said reservoir.

12. A device according to claim 3 wherein said delay membrane is polyvinyl alcohol.

13. A device according to claim 3 wherein said drug is nicotine.

14. A method for delaying delivery of a drug selected form the group consisting of nicotine and melatonin to the skin or mucosa, said method comprising the steps of:
    1) placing a delivery device onto the skin or mucosa, said device comprising;
        a backing layer impermeable to said drug;
        a drug-containing reservoir disposed between said backing layer and the skin or mucosa;
        a drug release delay membrane comprised of a hydrophilic or semihydrophilic polymer disposed between said reservoir and the skin or mucosa such that said drug must pass through said delay membrane to reach the skin or mucosa, said delay membrane being substantially free of undissolved drug and being impermeable to said drug when in a dry state and permeable to said drug when in a hydrated state; and means for maintaining said device in drug-transmitting relationship to the skin or mucosa; and 2) changing said delay membrane of said delivery device from said dry state to said hydrated state, whereby the passage of said drug from said reservoir to the skin or mucosa is delayed.

15. The method according to claim 14 wherein said delay membrane is changed from its dry state to its hydrated state after placement on the skin or mucosa.

16. The method according to claim 14 wherein said delay membrane is changed from its dry state to its hydrated state by cutaneous liquids.

17. The method according to claim 14 wherein said delivery device further comprises a rate-controlling membrane.

18. The method according to claim 14 wherein said delay membrane is polyvinyl alcohol.

19. The method according to claim 14 wherein said drug is nicotine.

20. A method for reducing the side effects associated with the transdermal delivery of nicotine during sleeping hours, said method comprising the steps of:

1) placing a delivery device onto the skin or mucosa prior to bedtime, said device comprising:

a backing layer impermeable to nicotine;

a nicotine-containing reservoir disposed between said backing layer and the skin or mucosa;

a nicotine release delay membrane comprising polyvinyl alcohol disposed between said reservoir and the skin or mucosa such that nicotine must pass through said delay membrane to reach the skin or mucosa, said delay membrane being substantially free of undissolved nicotine and being impermeable to nicotine when in a dry state and permeable to nicotine when in a hydrated state; and means for maintaining said device in nicotine-transmitting relationship to the skin or mucosa; and 2) changing said delay membrane of said delivery device from said dry state to said hydrated state, whereby the passage of nicotine from said reservoir to the skin or mucosa is delayed until shortly prior to awakening.

21. The method according to claim 20 wherein said delay membrane is changed from its dry state to its hydrated state after placement on the skin or mucosa.

22. The method according to claim 20 wherein said delay membrane is changed from its dry state to its hydrated state by cutaneous liquids.

23. The method according to claim 20 wherein said delivery device further comprises a rate-controlling membrane.

24. A method for relieving the early morning withdrawal symptoms associated with low plasma concentrations of nicotine during sleeping hours, said method comprising the steps of:

1) placing a delivery device onto the skin or mucosa prior to bedtime, said device comprising:

a backing layer impermeable to nicotine;

a nicotine-containing reservoir disposed between said backing layer and the skin or mucosa;

a nicotine release delay membrane comprising polyvinyl alcohol disposed between said reservoir and the skin or mucosa such that nicotine must pass through said delay membrane to reach the skin, said delay membrane being substantially free of undissolved nicotine and being impermeable to nicotine when in a dry state and permeable to nicotine when in a hydrated state; and means for maintaining said device in nicotine-transmitting relationship to the skin or mucosa; and 2) changing said delay membrane of said delivery device from said dry state to said hydrated state, whereby the passage of nicotine from said reservoir to the skin or mucosa is delayed until shortly prior to awakening, whereby therapeutic plasma levels of nicotine are present at the time of awakening.

25. The method according to claim 24 wherein said delay membrane is changed from its dry state to its hydrated state after placement on the skin or mucosa.

26. The method according to claim 24 wherein said delay membrane is changed from its dry state to its hydrated state by cutaneous liquids.

27. The method according to claim 24 wherein said delivery device further comprises a rate-controlling membrane.

* * * * *